United States Patent [19]

Lin

[11] Patent Number: 4,486,593
[45] Date of Patent: Dec. 4, 1984

[54] 2-,3-, OR 4-PYRIDINYLMETHYLAMINO ARYLIC ACIDS AS THROMBOXANE $A_2$ SYNTHETASE AND 5-LIPOXYGENASE INHIBITORS

[75] Inventor: Chiu-Hong Lin, Portage, Mich.

[73] Assignee: The Upjohn Company, Kalamazoo, Mich.

[21] Appl. No.: 459,074

[22] Filed: Jan. 19, 1983

[51] Int. Cl.$^3$ .................. C07D 401/12; C07D 213/55
[52] U.S. Cl. ..................................... 546/335; 546/276; 546/334; 546/332; 546/329; 546/337
[58] Field of Search ................................ 546/276, 335

[56] References Cited

U.S. PATENT DOCUMENTS

| 3,646,045 | 2/1972 | Berger et al. | 546/329 |
| 3,654,290 | 4/1972 | Berger | 260/296 R |
| 4,112,224 | 9/1978 | Bundy | 542/426 |

FOREIGN PATENT DOCUMENTS

| 0000176 | 1/1979 | European Pat. Off. |
| 1585082 | 1/1970 | France . |
| 50-111076 | 9/1975 | Japan . |
| 2039903A | 8/1980 | United Kingdom . |

OTHER PUBLICATIONS

DiFonzo et al., Chem. Abst., 21789n, (1967).
D. Harris, et al., Advances in Prostaglandin and Thromboxane Research, 6:437, (1980).
T. Miyamoto, et al., Advances in Prostaglandin and Thromboxane Research, 6:443, (1980).
H. Tai, et al., Advances in Prostaglandin and Thromboxane Research, 6:447, (1980).
Denny, et al., J. Med. Chem. 20:1242, (1977).
Derwent Farmdoc No. 20536F, (1966).
Derwent Farmdoc No. 29402F, (1967).
Derwent Farmdoc No. 11056T, (1972).
Derwent Agdoc No. 06401A, (1978).
Derwent Farmdoc No. 11911B, (1977).
Derwent Farmdoc No. 12380B, (1979).
Derwent Agdoc No. 50291C, (1980).
Chemical Abstracts, 86:171350U, (1976).
Derwent Agdoc No. 75975R, (1970).
Derwent Farmdoc No. 75002U, (1975).
Derwent Farmdoc No. 03847D, (1981).

Primary Examiner—Henry R. Jiles
Assistant Examiner—Bernard L. Dentz
Attorney, Agent, or Firm—Lawrence T. Welch

[57] ABSTRACT

The present invention provides novel 2-, 3-, or 4-pyridinylmethylamino arylic acids which are useful as thromboxane $A_2$ (TXA$_2$) synthetase inhibitors and 5-lipoxygenase inhibitors and as such represent useful pharmacological agents.

16 Claims, No Drawings

2-, 3-, OR 4-PYRIDINYLMETHYLAMINO ARYLIC ACIDS AS THROMBOXANE $A_2$ SYNTHETASE AND 5-LIPOXYGENASE INHIBITORS

DESCRIPTION

BACKGROUND OF THE INVENTION

The present invention relates to novel compositions of matter. More particularly, the present invention relates to 2-, 3-, or 4-pyridinylmethylamino arylic acids. These compounds are potent thromboxane $A_2$ synthetase inhibitors and/or 5-lipoxygenase inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

In mammalian metabolism, arachidonic acid is transformed to 12-L-hydroperoxy-5,8,10,14-eicosatetraenoic acid by the action of 12-lipoxygenase. See, Hamberg, et al, Proc. Nat. Acad. Sci. 71:3400–3404 (1974). Similarly, 5-lipoxygenase transforms arachidonic acid into 5-S-hydroperoxy-6,8,11,14-eicosatetraenoic acid. Thus, an agent which inhibits the action of lipoxygenase would be useful in treating or preventing untoward conditions associated with lipoxygenase products.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds of thromboxane synthetase is very weak making them unsatisfactory as practically effective medicines.

French Pat. No. 1,585,085 (Derwent Farmdoc 40389R) discloses certain N-pyridinyl/anthranilic acids which are stated to be useful as analgesic, antipyretic, anti-inflammatory and anti-rheumatic agents. Japanese Kokai No. 75 111,076 (Derwent Farmdoc 1024X) discloses certain pyridyloxy-phenylalkanoic or pyridyloxy-benzoic acid derivatives which are stated to be useful as anti-inflammatory, anti-rheumatic and analgesic agents. European Pat. No. 176 (Derwent Farmdoc 02309B) discloses certain pyridyloxy-phenoxy-alkanoic acid derivatives which are stated to be useful as herbicides and plant growth regulators. Denny, et al., J. Med. Chem. 20:1242 (1977) discloses pyridinyl anthranilic acids.

Certain 2-pyridinyl-phenylene compounds are disclosed in Derwent Farmdoc nos. 20536F; 29402F; 11056T; 06401A; 11911B; 12380B; and 50291C; and C.A. 86:17135U. Other pyridinyl-phenylene compounds are disclosed in Derwent Farmdoc Nos. 75975R; 75002U; and 03847D.

Certain 3-pyridinyl-δ-carboxylic acids having aza and phenylene groups in the side chain are disclosed in copending application Ser. No. 402,514, filed July 28, 1982. U.S. Pat. No. 3,654,290 discloses certain N-amino-N-arylaminoalkylpyridinesas intermediates for the preparation of certain 5-(pyridylalkyl)pyridoindole derivatives having antiallergic activity.

Copending application Ser. No. 350,553, filed Feb. 19, 1982 and Ser. No. 431,906, filed Sept. 30, 1982 disclose certain phenyl hydrazones and phenyl hydrazines as lipoxygenase inhibitors.

SUMMARY OF THE INVENTION

The present invention particularly provides: a compound of the formula I or a pharmacologically acceptable acid addition salt thereof,
 wherein $Z_1$ is 2-, 3-, or 4-pyridyl;
 wherein $Z_1$—$(CH_2)_m$—NH— is attached ortho, meta or para to —$Y_1$—$(CH_2)_n$—$Q_1$;
 wherein $Y_1$ is
  (a) —O—,
  (b) —S—,
  (c) —$NR_3$—, or
  (d) a valence bond;
 wherein $R_2$ is
  (a) hydrogen,
  (b) hydroxy,
  (c) methoxy,
  (d) acetoxy,
  (e) fluoro,
  (f) chloro,
  (g) bromo,
  (h) methyl,
  (i) trifluoromethyl,
  (j) dimethylamino, or
  (k) nitro,
  (l) mercapto, or
  (m) methylmercapto;
 wherein $Q_1$ is
  (a) —$CO_2R_1$,
  (b) —$CH_2OH$,
  (c) —$CH_2SH$,
  (d) —$NR_3$, or
  (e) 1-tetrazolyl;
 wherein $R_1$ is
  (a) hydrogen,
  (b) a pharmacologically acceptable cation,
  (c) ($C_1$–$C_{12}$) alkyl,
  (d) ($C_3$–$C_{10}$) cycloalkyl,
  (e) ($C_7$–$C_{12}$) aralkyl,
  (f) phenyl,
  (g) phenyl mono-, di-, or trisubstituted by chloro, or ($C_1$–$C_3$) or alkyl, or
  (h) phenyl para-substituted by (1) —NHCO—$R_{25}$,
(2) —O—CO—$R_{26}$,
(3) —CO—$R_{24}$,
(4) —O—CO—(p—Ph)—$R_{27}$, or
(5) —CH=N—NH—CO—$NH_2$, wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy, $R_{27}$ is hydrogen or acetamido, and —(p—Ph) is 1,4-phenylene;

wherein $R_3$ is
(a) hydrogen
(b) ($C_1$-$C_5$)alkyl, or
(c) —CHO;

wherein m is an integer from zero to 6, inclusive;

wherein n is an integer from zero to 6, inclusive, with the proviso that n is zero only when $Y_1$ is a valence bond and $Q_1$ is —$CO_2R_1$ or 1-tetrazolyl.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit TXA$_2$ synthetase are found. For a discussion of TXA$_2$ synthetase inhibition testing see, e.g., R. Gorman, supra.

Using this test system, 4-(3-pyridinylmethylamino)-salicyclic acid, sodium salt (Example 2) has been shown to be the most effective in inhibiting TXA$_2$ formation. This compound has an approximate ED$_{50}$ in this system of between 10 and 100 ng/ml.

The compounds of the present invention were also tested for 5-lipoxygenase inhibition. Arachidonic acid is added to washed human platlets and the oxygen uptake is measured using oxygraph cells. A decrease of oxygen uptake versus the control cell indicates inhibition of lipoxygenase. For a fuller description of the procedure see, Wallach, et al., Biochim. Biophys. Acta. 231:445 (1976).

Using this system, 5-(3-pyridinylmethylamino)salicyclic acid, methyl ester (example 3), has been shown to be the most effective, having an approximate ED$_{50}$ in this system of $1 \times 10^{-5}$ Molar.

Thus, some of the novel compounds of this invention have been shown to be active as inhibitors of the thromboxane synthetase enzyme system and some of the compounds of this invention have been shown to be active as inhibitors of the lipoxygenase enzyme system. Some of these compounds are effective in both systems. All of the compounds of this invention are active as inhibitors of at least one of these two systems. Accordingly, these novel compounds are useful for administration to mammals, including humans, whenever it is desirable medically to inhibit either of these enzyme systems.

Thromboxane synthetase inhibitors are useful to treat inflammation, to inhibit platelet aggregation, and to treat or prevent gastrointestinal ulcer formation. For a discussion of the utility of TXA$_2$ inhibitors, see, e.g., Derwent Farmdoc Nos. 18399B; 72896B; 72897B; 63409B; 03755C; 03768C; and 50111C.

Thromboxane synthetase converts PGH$_2$ (prostaglandin endoperoxide) into TXA$_2$. PGH$_2$ is also converted to prostacyclin, PGD$_2$, and other compounds by other enzymes. Thus, because the compounds of this invention inhibit thromboxane A$_2$ synthetase, they increase the PGH$_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of TXA$_2$ synthetase inhibitors which increase endogenous prostacyclin, see, Aiken, et al. J. Pharmacol. Exp. Ther., 219:299 (1981).

Lipoxygenase inhibitors are also useful as to treat inflammation and to inhibit platlet aggregation. Thus, Hammerström, et al. Science 197:994–996 (1977) notes the role of 12-lipoxygenase in psoriasis. Doig, et al., Prostaglandins 20:1007–1019 (1980) and Lin, et al., J. Clin. Invest. 70:1058 (1982) disclose that 5-lipoxygenase inhibitors block platlet thrombus formation. Dawson, et al., in SRS-A and Leukotrienes, 219–226 (wiley and Sons 1981) note that 5-lipoxygenase inhibitors block neutrophil "recruitment" during inflammatory diseases such as arthritis.

In addition, 5-lipoxygenase inhibitors may prevent the production of slow-reacting substance of anaphylaxis (SRS-A), now known to be a mixture of leukotrienes. (All leukotrienes are synthesized using 5-lipoxygenase.) SRS-A mediates the symptoms and pathophysiology of asthma. See Murphy, et al., Proc. Nat. Acad. Sci. USA 76, 4275–4279 (1979). Thus, the 5-lipoxygenase inhibitors disclosed herein may be useful in the treatment of asthma.

5-lipoxygenase products have been implicated in essential hypertension (Chand, et al., Microcirculation 1:111–123 (1981), and gout (Rae, et al., Lancet 1122–1124 (Nov. 20, 1982), indicating that the 5-lipoxygenase inhibitors disclosed herein are useful in treating these conditions as well. Further, neutrophil depletion, such as that induced by 5-lipoxygenase inhibitors, has been shown to cause a significant decrease in infarct size following circumflex artery occlusion. See Romson, et al., Circulation 66:85 (1982). Thus, the 5-lipoxygenase inhibitors herein may be useful in the protection of the myocardium following infarct.

All of the compounds of the present invention are TXA$_2$ synthetased inhibitors or 5-lipoxygenase inhibitors, and some have both properties. Thus, all of the compounds of this invention are useful as antiinflammatory agents and as platelet aggregation inhibitors. These are the preferred uses for these compounds.

Thus, for example, all of these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range of 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, to reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thus, the compounds are administered orally in forms such as pills, capsules, solutions or suspensions. They may also be administered rectally or vaginally in forms such as suppositories or bougies. They may also be introduced intravenously, subcutaneously, or intramuscularly using sterile injectable forms known to the pharmaceutical art.

In general the preferred form of administration is orally.

The compounds of the present invention are prepared by the methods depicted in Charts A, B, and C. In these charts, the compounds of formulas A-1, B-1, and C-1 are either available or synthesized via processes known in the art (see, J. B. Hendrickson, J. Amer. Chem. Soc., 93:6854 (1971)).

Chart A depicts a method for preparing compounds of the present invention wherein $Z_1$ is pyridine, $Y_1$ is a valence bond, and $Q_1$ is $-CO_2R_1$ (Formula I). An aminosalicyclic acid of the formula A-1 (a well known, readily available compound) is treated with diazomethane in methanol to yield the formula A-2 ester. This ester is then reacted with an aldehyde of the formula A-2A to yield the corresponding imines which are reduced with sodium borohydride to yield the corresponding formula A-3 compounds. These compounds are then converted to pharmacologically acceptable salts by means well known in the art, e.g., treatment with sodium hydroxide in methanol, to yield the formula A-4 compound. The process depicted in Chart A can be utilized for all definitions of $R_2$, i.e., when $R_2$ is other than hydroxy.

Chart B depicts a method for preparing compounds of the present invention wherein $Z_1$ is pyridine, $Y_1$ s $-O-$ or $-S-$ and $Q_1$ is $-CO_2R_1$ (formula I). A hydroxyaniline derivative of the formula B-1 is converted to a diacetate of the formula B-2 by means well known in the art, e.g., acetic anhydride in pyridine. The diacetate of the formula B-2 is selectively hydrolyzed utilizing potassium carbonate in methanol to form the acetamidophenol derivative of the formula B-3. Alkylation of the formula B-3 compound, utilizing sodium hydride or potassium carbonate as the base and dimethylformamide (DMF), glyme, tetrahydrofuran (THF), or acetone, as the solvent gives the formula B-4 product. Treatment of this Formula B-4 compound with strong acid such as hydrochloric acid in aqueous alcoholic solvent (see, e.g., Organic Synthesis, Coll. Vo. I, III) with or without heating affords the aniline derivative of the formula B-5. Condensation of this formula B-5 compound with an appropriate aldehyde of the formula B-5A yields the imine which is reduced with sodium borohydride to give the formula B-6 product. The corresponding pharmacologically acceptable salts may be prepared as described above. Chart B also depicts a method for preparing compounds of the present invention wherein $Z_1$ is pyridine, $Y_1$ is $-S-$, and $Q_1$ is $-CO_2R_1$ (Formula I). Starting from either the aminothiophenol derivative of the formula B-1 or the acetamidothiphenol derivative of the formula B-3, the compounds of the formula B-5, B-6, and B-7 can be prepared by the procedures described above.

Chart C depicts a method for preparing compounds of the present invention wherein $Z_1$ is pyridine, $Y_1$ is $-NH-$, and $Q_1$ is $-CO_2R_1$ (Formula I). A nitroaniline derivative of the formula C-1 is thermally condensed with an appropriate aldehyde of the formula C-1A to yield the imine which is reduced with sodium borohydride to yield the formula C-2 compound. Acetylation of the formula C-2 compound with acetic anhydride in pyridine yields the acetamide derivative of the formula C-3. The nitro group of the formula C-3 compound is reduced by methods known in the art (see, e.g., Compendium of Organic Synthetic Methods, Vol. 2, p. 104; Vol. 4, p. 162) to yield the aniline derivative of the formula C-4. Condensation of the formula C-4 compound with ω-formyl alkanoic acid, methyl ester (C-4A, e.g., the methyl ester of glyoxalic acid) to yield the amine which is reduced with sodium borohydride to yield the formula C-5 compound. Acidic hydrolysis of the formula C-5 compound as described above to remove the acetyl group yields the formula C-6 product. Alternatively the formula C-4 compound is acetylated to give the diacetate of the formula C-8. Alkylation of the formula C-8 compound as described in Chart B yields the alkylated C-9 compound. Acidic hydrolysis of the formula C-9 compound affords the formula C-6 product. Pharmacologically acceptable salts may be prepared as described above to yield the formula C-7 compound.

Certain compounds of the present invention are preferred. Thus, compounds of the formula I wherein $Y_1$ is a valence bond, n is zero, m is 1, and $Q_1$ is $-CO_2R_1$ are preferred. More preferred in this class of compounds are those compounds wherein $R_1$ is hydrogen or methyl and $R_2$ is hydrogen, hydroxy, methoxy, or acetoxy; wherein $R_1$ is hydrogen or methyl, and $R_2$ is fluoro or trifluoromethyl; wherein $R_1$ is a pharmacologically acceptable cation selected from the group consisting of sodium, potassium or calcium and $R_2$ is hydrogen, hydroxy, methyl or acetoxy; or wherein $R_1$ is a pharmacologically acceptable cation selected from sodium, potassium, or calcium and $R_2$ is fluoro or trifluoromethyl.

Another preferred class of compounds are those wherein $Y_1$ is —O—; m is 1; and $Q_1$ is —$CO_2R_1$. More preferred in this latter class of compounds are those wherein $R_1$ is hydrogen or methyl and $R_2$ is hydrogen, hydroxy, methoxy, or acetoxy; wherein $R_1$ is hydrogen or methyl, and $R_2$ is fluoro or trifluoromethyl; wherein $R_1$ is a pharmacologically acceptable cation selected from the group consisting of sodium, potassium or calcium and $R_2$ is hydrogen, hydroxy, methyl or acetoxy; or wherein $R_1$ is a pharmacologically acceptable cation selected from sodium, potassium, or calcium and $R_2$ is fluoro or trifluoromethyl.

4-(3-Pyridinylmethylamino)salicyclic acid, sodium salt (Example 2) and 5-(3-pyridinylmethylamino)salicyclic acid, methyl ester (Example 3) are the most preferred compounds of the present invention. ,0,,

DESCRIPTION OF THE PREFERRED EMBODIMENTS

The present invention is seen more fully by the Examples given below.

Preparation 1: 4-Aminosalicylic Acid, Methyl Ester

Refer to Chart A, (conversion of A-1 to A-2).

A round-bottomed flask equipped with a magnetic stirring bar is charged with 15.3 g (0.1 mol) of 4-aminoisalicylic acid and 100 ml of methanol. Freshly prepared diazomethane in ether is added until thin layer chromatography (TLC) indicates no starting material is remaining. The solvent is removed in vacuo and the residue is dissolved in hot ethyl acetate-hexane, decolorized with activated charcoal, filtered through a pad of celite, and concentrated in vacuo. The residue is recrystallized from the ethyl acetate-hexane. The first crop affords 12.43 g of the second crop 1.10 g for a total of 13.53 g (81%) of crystals having a melting point (mp) of 119°-120° C. NMR ($CDCl_3$, TMS, $\delta$) peaks are observed at 7.70-6.00, 4.10, and 3.86. TLC (silica gel GF), reveals an Rf of 0.39 in hexane-acetone (2:1).

Preparation 2: 5-Aminosalicylic Acid, Methyl Ester

Refer to Chart A (conversion of A-1 to A-2).

A round-bottomed flask equipped with a magnetic stirring bar is charged with 30.6 g (0.2 mol) of 5-aminosalicylic acid (Aldrich) and 200 ml of methanol. Freshly prepared diazomethane in ether is added until TLC indicates no starting material remains. After the removal of solvent in vacuo a black solid is obtained. This solid is subjected to column chromatography using 1.2 kg of silica gel (EM, 63–200$\mu$), eluting with methylene chloride-ethyl acetate (10:1), and collecting 300 ml fractions. Fractions (19-22) are homogeneous by TLC and are combined and concentrated in vacuo to give a brown oil (2.63 g). This material is less polar than the desired product and NMR reveals an extra peak at $\delta$ 2.80 as a singlet. Fractions (24–60) are homogeneous by TLC and are combined and concentrated in vacuo to give a yellow solid (31.8 g). Recrystallization from hexane-ethyl acetate affords 25.3 g (75.8%) of yellow crystals with a melting point of 95°-96° C.; NMR ($CDCl_3$, TMS, $\delta$) peaks are observed at 7.38-6.80 (-aryl-), 3.92, 10.28 and 3.50. TLC (silica gel GF), reveals an Rf of 0.45 in hexane-acetone (1:1).

EXAMPLE 1

4-(3-Pyridinylmethylamino)salicylic Acid, Methyl Ester (Formula I: $Z_1$ is 3-pyridyl; m is 1, $Z_1$—$(CH_2)_m$—NH is para, $R_2$ is ortho hydroxy, $Y_1$ is a valence bond, n is zero, and $Q_1$ is —$CO_2CH_3$)

A round-bottomed flask equipped with a magnetic stirring bar, a Dean-Stark moisture receiver, and a reflux condenser is charged with 3.34 g (20.0 mmol) of 4-aminosalicylic acid, methyl ester (Preparation 1) 2.14 g (20.0 mmol) of 3-pyridinecarboxaldehyde (Aldrich), 0.19 g (1.0 mmol) of p-toluenesulfonic acid, and 300 ml of benzene under a nitrogen atmosphere. The mixture is heated to reflux (bath temperature 110° C.) for 24 hours. The solvent is removed in vacuo and the residue is dissolved in 200 ml of methanol. The solution is cooled to 0°-5° C. and sodium borohydride powder (2.78 g, 60.0 mmol) is added over a period of 5 minutes. After stirring the mixture for one hour, the reaction is quenched with aqueous saturated ammonium chloride and the methanol is removed in vacuo. The residue is treated with brine and extracted with ethyl acetate (1L). The organic layer is washed with brine and dried over anhydrous magnesium sulfate. Filtration and concentration in vacuo afford a pale yellow solid. TLC analysis shows that the imine is not completely reduced. Therefore the solid is redissolved in 200 ml of methanol and reacted this time with 7.6 g (200.0 mmol) of sodium borohydride at 0°-5° C. After one hour, the mixture is worked up as above to give the crude product (4.6 g). Liquid chromatography is carried out by using 388 g of silica gel (EM, 40–63$\mu$), eluting with methylene chloride-acetone (4:1), and collecting 40 ml fractions. Fractions (15-22) are homogeneous by TLC and are combined and concentrated in vacuo to give 1.02 g (30%) of recovered starting material, 4-aminosalicyclic acid, methyl ester. Fractions (44-63) are homogeneous by TLC and are combined and concentrated in vacuo to give 2.40 g of the titled product. Recrystallization from hexane-ethyl acetate affords a white solid (a first crop of 1.89 g and a second crop of 0.26 g for a total of 2.14 g a 41% yield) with a melting point of 94°-95° C.

The NMR ($CD_3OD+D_2O$, TMS, $\delta$) reveals peaks at 8.70–6.08, 4.38, and 3.88.

The IR (Nujol, $\nu$max) reveals peaks at 3235, 3152, 3047, 3006, 2956, 1666, 1626, 1578, 1542, 1440, 1337, 1272, 1264, 1199, 1188, 1096, and 1031 cm$^{-1}$.

Mass Spectrum yields ions at m/e 258.0995, 226, 211, 197, 180, 169, 148, 136, 106, and 92.

C:H:N Analysis yields: Calcd. for $C_{14}H_{14}N_2O_3$: C, 65.10; H, 5.46; N, 10.85; Found: C, 64.73; H, 5.46; N, 10.71.

TLC Analysis (Silica Gel GF) yields an Rf of 0.34 in methylene chloride-acetone (2:1).

EXAMPLE 2

4-(3-Pyridinylmethylamino)salicylic Acid, Sodium Salt (The sodium salt of Example 1)

A round-bottomed flask equipped with a magnetic stirring bar is charged with 516.6 mg (2.0 mmol) of the compound of Example 1, 2.0 ml (2.0 mmol) of 1N aqueous sodium hydroxide, and 4.0 ml of methanol. The resulting yellow solution is stirred at room temperature for 24 hrous. TLC analysis shows no reaction occurs. Therefore 2.0 ml (2.0 mmol) of 1N aqueous sodium hydroxide and 2.0 ml of methanol are added and the solution is stirred for an additional 24 hours. TLC analysis shows only about 50% completion. Another portion of 2.0 ml (2.0 mmol) of 1N aqueous sodium hydroxide and 2.0 ml of methanol is added. The mixture is heated at 50° C. and stirred for 48 hr. TLC analysis shows no starting material remaining. Methanol-water is removed in vacuo and the residue is dissolved in about 10 ml of water and then the solution is diluted with 600 ml of acetone and the cloudy solution is allowed to stand in the refrigerator for 2 days. The solution is filtered and concentrated in vacuo. The residue is treated with toluene-acetone and the resulting light red solid is separated. The red solid is dried in vacuo to obtain 503.0 mg of the titled sodium salt.

NMR (CDCl$_3$, TMS, δ) reveals peaks at 8.72–6.00 and 4.43.

IR (Nujol, νmax) reveals peaks at 3357, 2954, 1635, 1589, 1583, 1562, 1484, 1439, 1433, 1386, 1356, 1333, 1329, 1201, 1192, 1167, 835 and 769 cm$^{-1}$.

TLC Analysis (Silica Gel GF) yields an Rf of 0.03 in methylene chloride-acetone (2:1).

EXAMPLE 3

5-(3-Pyridinylmethylamino)salicylic Acid, Methyl Ester (Formula I: $Z_1$ is 3-pyridyl, m is 1, $Z_1$—$(CH_2)_m$—NH— is meta, $R_2$ is ortho hydroxy, $Y_1$ is a valence bond, n is zero, and $Q_1$ is —$CO_2CH_3$)

Refer to Chart A (conversion of A-2 to A-3).

A round-bottomed flask equipped with a magnetic stirring bar, a Dean-Stark moisture receiver, and a reflux condenser is charged with 3.34 g (20.0 mmol) of 5-aminosalicylic acid, methyl ester (Preparation 2), 2.14 g (20.0 mmol) of 3-pyridinecarboxaldehyde (Aldrich), 0.19 g (1.0 mmol) of p-toluenesulfonic acid, and 120 ml of benzene-glyme (5:1) under a nitrogen atmosphere. The mixture is heated to reflux (bath temperature, 110° C.) for 2 hours. TLC shows no starting material remaining. The solvent is removed in vacuo to give a brown oil. This oil is dissolved in 120 ml of methanol and the solution is cooled to 0°–5° C. with an ice-water bath. Sodium borohydride powder (2.28 g, 60.0 mmol) is added over a period of 5 minutes under a nitrogen atmosphere. The resulting light brown solution is stirred for one hour. TLC shows no starting material remaining. The reaction is quenched with 50 ml of saturated aqueous ammonium chloride and the methanol is removed in vacuo. The residue is treated with 50 ml of 1N aqueous sodium hydroxide and extracted twice with 400 ml of ethyl acetate. The organic layer is washed with 20 ml of 1N aqueous sodium hydroxide, brine, and dried over anhydrous magnesium sulfate. Filtration and concentration afford a brown oil. Liquid chromotography is carried out by using 166 g of silica gel (EM, 40–63µ), eluting with methylene chloride-acetone (4:1), and collecting 30 ml fractions. Fractions (26–53) are homogeneous by TLC and are combined and concentrated in vacuo to give a yellow solid. Recrystallization from hexane-ethyl acetate affords a yellow solid (4.10 g, 79.3%) with a melting point of 79°–80° C.

The NMR (CDCl$_3$, TMS, δ) reveals peaks at 8.75–6.84, 4.32, and 3.90.

The IR (Nujol, νmax) reveals peaks at 3310, 3245, 1685, 1620, 1530, 1450, 1290, 1235, 1180, 1075, 785 and 710 cm$^{-1}$.

The Mass Spectrum yields ions at m/e 258.0990, 226, 197, 181, 169, 148, 134, 120, 106, and 92.

C:H:N Analysis yields: Calcd. for $C_{14}H_{14}N_2O_3$: C, 65.10; H, 5.46; N, 10.85. Found: C, 64.84; H, 5.49; N, 10.69.

TLC Analysis (Silica Gel GF) yields an Rf of 0.33 in methylene chloride-acetone (2:1).

EXAMPLE 4

5-(3-Pyridinylmethylamino)salicylic Acid, Sodium Salt (The sodium salt of Example 3)

A round-bottomed flask equipped with a magnetic stirring bar is charged with 1.3 g (5.0 mmol) of the compound of Example 3, 5.1 ml (5.1 mmol) of 1N aqueous sodium hydroxide, and 5.1 ml of methanol under a nitrogen atmosphere. The mixture is stirred at room temperature for 5 days. The solution turns deep brown in color. The mixture is lyophilized and the solid is washed with acetone to give 520 mg of a dark brown solid.

The NMR (CDCl$_3$+D$_2$O, TMS, δ) yields peaks at 8.75–6.84 and 4.42.

TLC Analysis (Silica Gel GF) reveals an Rf of 0.02 in methylene chloride-acetone (2:1).

EXAMPLE 5

5-(2-Pyridinylmethylamino)salicylic Acid, Methyl Ester (Formula I: $Z_1$ is 2-pyridyl, $Z_1$—$(CH_2)_m$—NH is meta, $R_2$ is ortho hydroxy, $Y_1$ is a valence bond, n is zero, and $Q_1$ is —$CO_2CH_3$)

Refer to Chart A (conversion of A-2 to A-3).

A round-bottomed flask equipped with a magnetic stirring bar, a Dean-Stark moisture receiver, and a condenser, is charged with 3.34 g (20 mmol) of the compound of Preparation 2, 2.14 g (20 mmol) of 2-pyridinecarboxaldehyde, 0.19 g (1.0 mmol) of p-toluene sulfonic acid, and 120 ml of benzene-glyme (5:1). The resulting deep brown solution is heated for 3 hours. TLC analysis shows no starting material remaining. The solvent is removed in vacuo to give a brown oil. The oil is dissolved in 100 ml of methanol and the solution is cooled to −20° ~ −10° C. under a nitrogen atmosphere. Sodium borohydride powder (2.28 g, 60 mmol) is added over a period of 5 minutes. After stirring for 30 minutes. TLC analysis shows no starting material remaining. The reaction is quenched with 50 ml of saturated aqueous ammonium chloride and methanol is removed in vacuo. The residue is extracted with 500 ml of ethyl acetate. The organic layer is washed with 1N aqueous sodium hydroxide (50 ml), brine, and dried over anhydrous magnesium sulfate. Filtration and concentration afford a brown oil. Purification is carried out by liquid chromatography, using 388 g of silica gel (EM, 40–63µ), eluting with methylene chloride-acetone (10:1), and collecting 40 ml fractions. Fractions (58–60) are homogeneous by TLC and are combined and concentrated in vacuo to give 4.06 g of crude titled product. Recrystallization from hexane-ethyl acetate affords a yellow solid (3.87 g, 75%) with a melting point of 84°–85° C.

The NMR (CDCl$_3$, TMS, δ) reveals peaks at 10.26, 4.58, 8.72–6.80, 4.40 and 3.96.

The Mass Spectrum yields ions at m/e 258.1010, 266, 198, 169, and 93.

C:H:N Analysis yields: Calcd. for $C_{14}H_{14}N_2O_3$: C, 65.10; H, 5.46; N, 10.85. Found: C, 64.92; H, 5.52; N, 10.84.

TLC Analysis (Silica Gel GF) yields an Rf of 0.5 in methylene chloride-acetone (2:1).

EXAMPLE 6

5-(2-Pyridinylmethylamino)salicyclic Acid, Sodium Salt (the sodium salt of Example 5)

A round-bottomed flask equipped with a magnetic stirring bar is charged with 1.29 g (5.0 mmol) of the compound of Example 5, 5.1 ml (5.1 mmol) of 1N aqueous sodium hydroxide and 5.1 ml of methanol. The resulting deep red solution is stirred at room temperature under a nitrogen atmosphere for 48 hours. TLC shows no starting material remains. The mixture is lyophilized. The solid is stirred in hot acetone and then the acetone is removed by filtration. The titled sodium salt is isolated as a light red solid (510 mg).

The NMR Spectrum (CD$_3$OD+D$_2$O, TMS, δ) reveals peaks at 8.83–6.63 and 4.46.

TLC Analysis (Silica Gel GF) yields an Rf of 0.01 in methylene chloride-acetone (2:1).

EXAMPLE 7

5-(4-Pyridinylmethylamine)salicyclic Acid, Methyl Ester (Formula I: $Z_1$ is 4-pyridyl, $Z_1$ is 4-pyridyl, $Z_1$—(CH$_2$)$_m$—NH is meta, $R_2$ is ortho hydroxy, $Y_1$ is a valence bond, n is zero, and $Q_1$ is CO$_2$CH$_3$)

Refer to Chart A (conversion of A-2 to A-3).

A round-bottomed flask equipped with a magnetic stirring bar, a Dean-Stark moisture receiver, and reflux condenser is charged with 3.34 g (20.0 mmol) of 5-aminosalicyclic acid, methyl ester (Preparation 2), 2.14 g (20.0 mmol) of 4-pyridinecarboxaldehyde (Aldrich), 0.19 g (1.0 mmol) of p-toluene sulfonic acid, and 120 ml of benzene-glyme (5:1) under a nitrogen atmosphere. The mixture is heated to reflux (bath temperature, 110° C.) for 2 hours. The solvent is removed in vacuo to give the imine. This imine is dissolved in 120 ml of methanol and the solution is cooled to 0°–5° C. with an ice-water bath. sodium borohydride powder (2.28 g, 60.0 mmol) is added over a period of 5 minutes under a nitrogen atmosphere. The resulting solution is stirred for one hour. The reaction is quenched with 50 ml of saturated aqueous ammonium chloride and the methanol is removed in vacuo. The residue is treated with 50 ml of 1N aqueous sodium hydroxide and extracted twice with 400 ml of ethyl acetate. The organic layer is washed with 20 ml of 1N aqueous sodium hydroxide, brine, and dried over anhydrous magnesium sulfate. Filtration and concentration afford the crude product. Liquid chromatography followed by recrystallization afford the titled product.

EXAMPLE 8

5-(4-Pyridinylmethylamino)salicyclic Acid, Sodium Salt (The sodium salt of Example 7)

A round-bottomed falsk equipped with a magnetic stirring bar is charged with 1.3 g (5.0 mmol) of the compound of Example 7, 5.1 ml (5.1 mmol) of 1N aqueous sodium hydroxide, and 5.1 ml of methanol under a nitrogen atmosphere. The mixture is stirred at room temperature until TLC analysis shows no starting material remaining. The mixture is lyophilized and recrystallized from acetone-water to give the titled product.

Preparation 3: 4-Acetamido-2-methyl-phenylacetate

Refer to Chart B (conversion of B-1 to B-2 wherein $R_2$ is ortho—CH$_3$, $Y_1$ is —O—).

A round-bottomed flask equipped with a magnetic stirring bar is charged with 12.3 g (0.1 mol) of 4-amino-o-cresol (Aldrich), 40 ml of acetic anhydride, and 40 ml of pyridine. The resulting mixture is stirred at room temperature until TLC shows no starting material remaining. The solution is cooled to 0°–5° C. with an ice-water bath and treated with 10 ml of water. After stirring the mixture for 30 minutes, saturated aqueous sodium bicarbonate is added slowly until the pH of the mixture reads 7–8. Extraction with ethyl acetate is followed by washing the organic layer with water and brine. Drying over anhydrous magnesium sulfate, filtration, and concentration in vacuo afford the crude product. Purification is carried out by chromatography or crystallization to give the titled product.

Preparation 4: 4-Acetamido-2-methyl-phenol

Refer to Chart B (conversion of B-2 to B-3 wherein $R_2$ is ortho—CH$_3$, $Y_1$ is —O—).

A round-bottomed flask equipped with a magnetic stirring bar is charged with 20.7 g (0.1 mol) of 4-acetamido-2-methyl-phenyl acetate (Preparation 3), 20.7 g (0.15 mol) of potassium carbonate, and 1 L of methanol. The resulting mixture is stirred at room temperature under a nitrogen atmosphere for 24 hours. Methanol is removed in vacuo and the residue is neutralized with 10% aqueous sodium bisulfate to pH~7. The mixture is extracted with ethyl acetate. The organic layer is washed with brine and dried over anhydrous magnesium sulfate. Filtration and concentration afford the crude product which is purified by either recrystallization or chromatography to give the titled product.

Preparation 5: 4-Acetamido-2-methyl-phenoxy Acetic Acid, Methyl Ester

Refer to Chart B (conversion of B-3 to B-4 wherein $R_2$ is ortho—CH$_3$, $Y_1$ is —O—).

A round-bottomed flask equipped with a magnetic stirring bar is charged with 16.4 g (0.1 mol) of 4-acetamido-2-methyl-phenol (Preparation 4), 16.5 g (0.12 mol) of potassium carbonate, 30.6 g (0.2 mol) of bromoacetate (Aldrich), and 200 ml of glyme. The mixture is stirred at room temperature for 24 hours. Glyme is removed in vacuo and the residue is neutralized with cold 10% aqueous sodium bisulfate until the pH of the mixture is 7–8. The mixture is extracted with ethyl acetate. The organic layer is washed with brine and dried over anhydrous magneisum sulfate. Filtration and concentration afford the crude product which is purified by either recrystallization or chromatography to give the titled product.

Preparation 6: (4-Amino-2-methyl-phenoxy)-phenoxy)-acetic Acid, Methyl Ester

Refer to Chart B (conversion of B-4 to B-5 wherein $R_2$ is ortho—CH$_3$, $Y_1$ is —O—, n is 1).

A round-bottomed flask equipped with a magnetic stirring bar and a reflux condenser is charged with 23.1 g (0.1 mol) of (4-Acetamido-2-methyl-phenoxy)-acetic acid, methyl ester (Preparation 5), 25 ml of 95% ethanol and 25 ml of concentrated hydrochloric acid (Organic Synthesis. Coll. Vol. I, III). The mixture is refluxed until TLC shows no starting material remaining. Concentration in vacuo is followed by neutralization of the mixture with 6N sodium hydroxide until the pH reaches 7–8. The amino acid thus obtained is purified by recrystallization or chromatography. This product is then methylated with diazomethane as described in Preparation 1 and 2. Purification affords the titled product.

EXAMPLE 9

[4-(3-Pyridinylmethylamino)-2-methyl-phenoxy]-acetic Acid, Methyl Ester

Refer to Chart B (conversion of B-5 to B-6 wherein m is 1, $R_2$ is ortho —$CH_3$, $Y_1$ is —O—, n is 1).

A round-bottomed flask equipped with a magnetic stirring bar, a Dean-Stark moisture receiver, and a reflux condenser is charged with 1.95 g (10 mmol) of (4-amino-2-methyl-phenoxy)-acetic acid, methyl ester (Preparation 6) 1.07 g (10 mmol) of p-toluene sulfonic acid, and 60 ml of benzene-glyme (5:1). The resulting solution is heated at reflux temperature until TLC analysis shows no starting material remaining. The solvent is removed in vacuo and the residue is dissolved in 50 ml of methanol and is cooled to 0°–5° C. Sodium borohydride powder (1.14 g, 30 mmol) is added over a period of 5 minutes. After stirring until TLC analysis shows no starting material remaining, the reaction is quenched with 25 ml of saturated aqueous ammonium chloride and the methanol is removed in vacuo. The residue is extracted with ethyl acetate and the organic layer is washed with 1N aqueous sodium hydroxide, brine, and dried over anhydrous magnesium sulfate. Filtration and concentration afford the crude product which is purified either by chromatography or recrystallization to give the titled product.

EXAMPLE 10

[4-(3-Pyridinylmethylamino)-2-methyl-phenoxy]-acetic Acid, Sodium Salt (The sodium salt of Example 9)

A round-bottomed flask equipped with a magnetic stirring bar is charged with 1.4 g (5.0 mmol) of the compound of Example 9, 5.1 ml (5.1 mmol) of 1N aqueous sodium hydroxide, and 5.1 ml of methanol under a nitrogen atmosphere. The mixture is stirred at room temperature until TLC analysis shows no starting material remaining. The mixture is lyophilized and recrystallized from acetone-water (or acetonitrile-water) to give the titled product.

Preparation 7: 4-Acetamidothiphenoxy-acetic Acid, Methyl Ester

Refer to Chart B (conversion of B-3 to B-4 wherein $R_2$ is —H, $Y_1$ is —S), n is 1).

A round-bottomed flask equipped with a magnetic stirring bar is charged with 16.7 g (0.1 mol) of 4-acetamidothiophenol (Aldrich), 16.6 g (0.12 mol) of potassium carbonate, 30.6 g (0.2 mol) of bromoacetate (Aldrich), and 200 ml of glyme. The mixture is stirred at room temperature until TLC analysis shows no starting material. Work-up is undertaken as described in Preparation 5 to give the titled product.

Preparation 8: (4-Amino-thiophenoxy)-acetic Acid, Methyl Ester

Refer to Chart B (conversion of B-4 to B-5 wherein $R_2$ is —H, $Y_1$ is —S—, n is 1)

Following the procedure described in Preparation 6, 4-acetamidothiophenoxy-acetic acid, methyl ester (Preparation 7) is converted to the titled product.

EXAMPLE 11

[4-(3-Pyridinylmethylamino)thiophenoxy]-acetic Acid, Methyl Ester

Refer to Chart B (conversion of B-5 to B-6 wherien m is 1, $R_2$ is —H, $Y_1$ is —S—, n is 1).

Following the procedure described in Example 9, (4-aminothiophenoxy)-acetic acid, methyl ester (Preparation 8) is reacted with 3-pyridinecarboxaldehyde (B-5A wherein m is 1) to yield the titled product.

EXAMPLE 12

[4-(3-Pyridinylmethylamino)-thiophenoxy]-acetic Acid, Sodium Salt

Refer to Chart B (conversion of B-6 to B-7 wherein m is 1, $R_2$ is —H, $Y_1$ is —S—, n is 1).

Following the procedure described in Example 10, [5-(3-pyridinylmethylamino)-thiophenoxy]-acetic acid methyl ester (Example 11) is converted to the titled product.

Preparation 9: 5-(3-Pyridinylmethylamino)-2-hydroxy-nitrobenzene

Refer to Chart C (conversion of C-1 to C-2 wherein m is 1, $R_2$ is —OH).

Following the procedure described in Example 9, 4-amino-2-nitrophenol (aldrich) is reacted with 3-pyridinecarboxaldehyde (C-1A wherein m is 1) to yield the titled product.

Preparation 10: 5-(3-Pyridinylmethylamino-N-acetyl)-2-acetoxynitrobenzene

Refer to Chart C (conversion of C-2 to C-3 wherein m is 1, $R_2$ is —OAc).

Following the procedure described in Preparation 3, 5-(3-pyridinylmethylamino)-2-hydroxy-nitrobenzene (Preparation 9) is converted to the titled product.

Preparation 11: 5-(3-Pyridinylmethylamino-N-acetyl)-2-acetoxyaminobenzene

Refer to Chart C (conversion of C-3 to C-4 wherein m is 1, $R_2$ is —OAc).

Following procedures known in the art (e.g., $Et_3N.HCO_2H$, Pt/C or $H_2$/Ru catalyst), the nitro group in (3-pyridinylmethyl amino-N-acetyl)-2-acetoxy-nitrobenzene (Preparation 10) is reduced to an amino group to yield the titled product.

Preparation 12: 5-(3-Pyridinylmethylamino-N-acetyl)-2-hydroxyaminobenzene-N-acetic Acid, Methyl Ester Refer to Chart C (conversion of C-4 to C-5 wherien m is 1, $R_2$ is —OH, n is 1).

Following the procedure described in Preparation 3, 5-(3-pyridinylmethylamino-N-acetyl)-2-acetoxy-aminobenzene (Preparation 11) is thermally condensed with the methyl ester of glyoxalic acid (C-4A wherein n is 1, $R_1$ is —$CH_3$) to yield the corresponding imine which is reduced with sodium borohydride to yield the titled product. The acetoxy group attached to the benzene ring is also hydrolyzed by sodium borohydride.

EXAMPLE 13

5-(3-Pyridinylmethylamino)-2-hydroxy-aminobenzene-N-acetic Acid, Methyl Ester

Refer to Chart C (conversion of C-5 to C-6 wherein m is 1, $R_2$ is —OH, n is 1).

Following the procedure described in preparation 6, 5-(3-pyridinylmethyl(amino-N-acetyl)-2-hydroxy-aminobenzene-N-acetic acid, methyl ester (Preparation 12) is converted to the titled product.

EXAMPLE 14

5-(3-Pyridinylmethylamino)-2-hydroxy-aminobenzene-N-acetic Acid, Sodium Salt

Refer to Chart C (conversion of C-6 to C-7 wherein m is 1, $R_2$ is —OH, n is 1).

Following the procedure described in Example 2, 5-(3-pyridinylmethylamino)-2-hydroxy-aminobenzene-N-acetic acid, methyl ester, is converted to the titled product.

EXAMPLE 13

5-(3-Pyridinylmethylamino-N-acetyl)-2-acetoxy-N-acetylaminobenzene

Refer to Chart C (conversion of C-4 to C-8 wherein m is 1, $R_2$ is —OAc).

Following the procedure described in Preparation 3, 5-(3-pyridinylmethylamino-N-acetyl)-2-acetoxy-aminobenzene (Preparation 11) is converted to the titled product.

Preparation 14:

5-(3-Pyridinylmethylamino-N-acetyl)-2-acetoxy-N-acetyl-aminobenzene-N-acetic Acid, Methyl Ester Refer to Chart C (conversion of C-8 to C-9 wherein m is 1, $R_2$ is —OAc).

Utilizing sodium hydride as the base and DMF as the solvent, the anion of 5-(3-pyridinylmethylamino-N-acetyl)-2-acetoxy-N-acetylaminobenzene (Preparation 13) is alkylated with bromoacetate (Aldrich) to give the titled product.

EXAMPLE 15

5-(3-Pyridinylmethylamino)-2-hydroxy-aminobenzene-N-acetic Acid, Methyl Ester

Refer to Chart C (conversion of C-9 to C-6 wherein m is 1, $R_2$ is —OH, n is 1).

Following the procedure described in Example 13, 5-(3-pyridinylmethylamino-N-acetyl)-2-acetoxy-N-acetyl-aminobenzene-N-acetic acid, methyl ester, (Preparation 14) is converted to the titled product.

FORMULA I

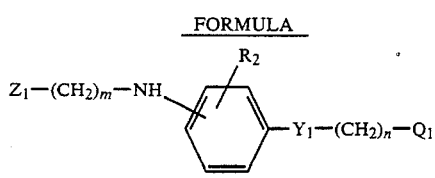

CHART A

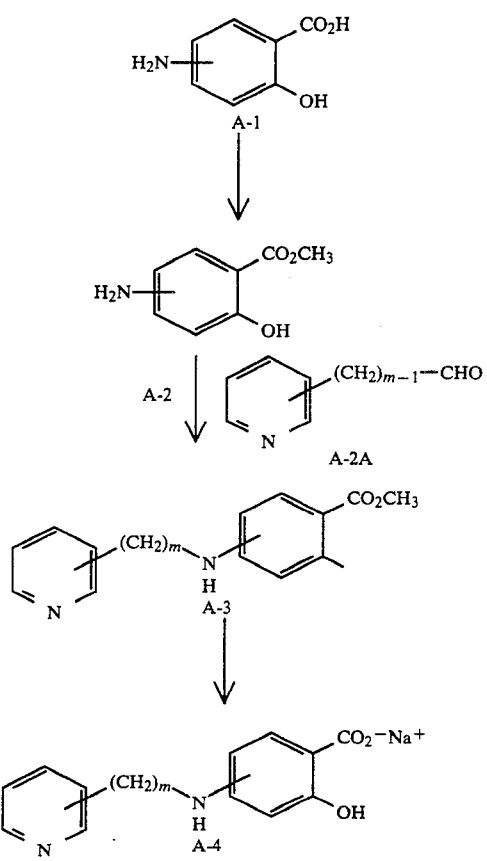

CHART B

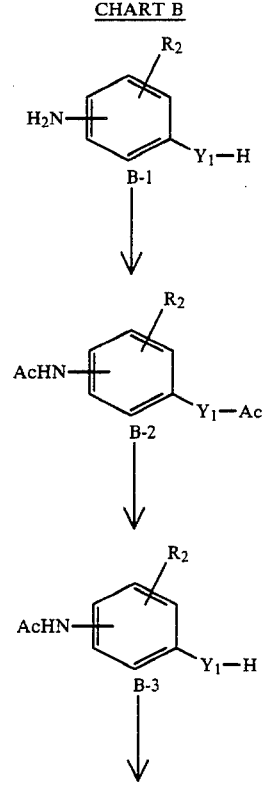

-continued
CHART B
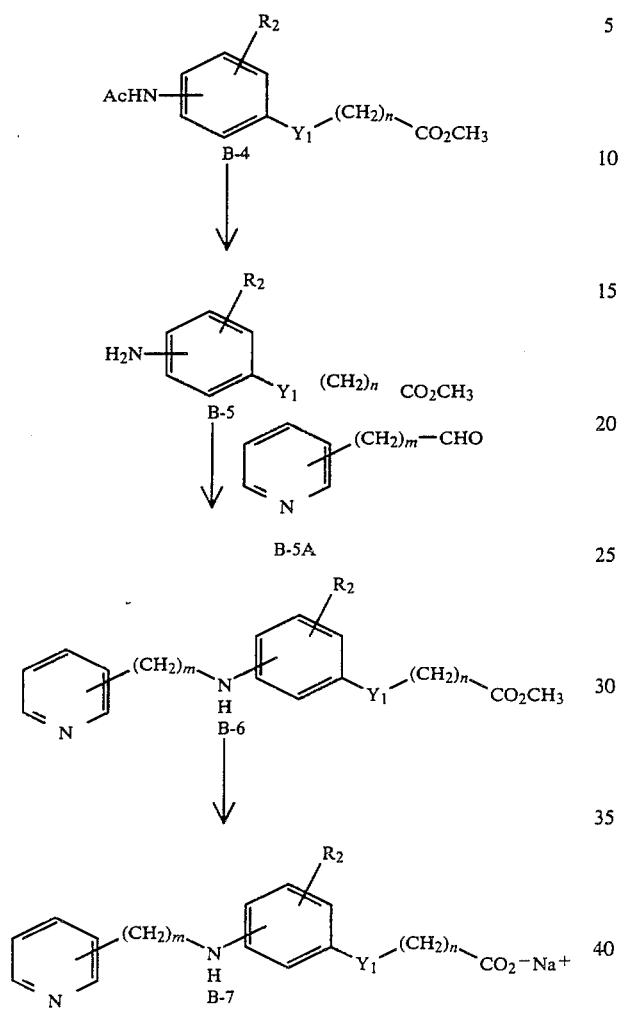
CHART C
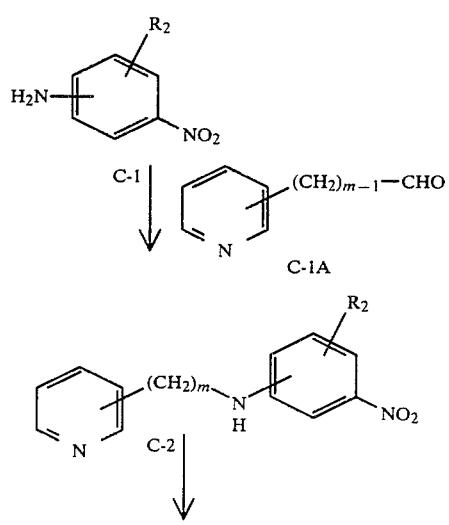
-continued
CHART C
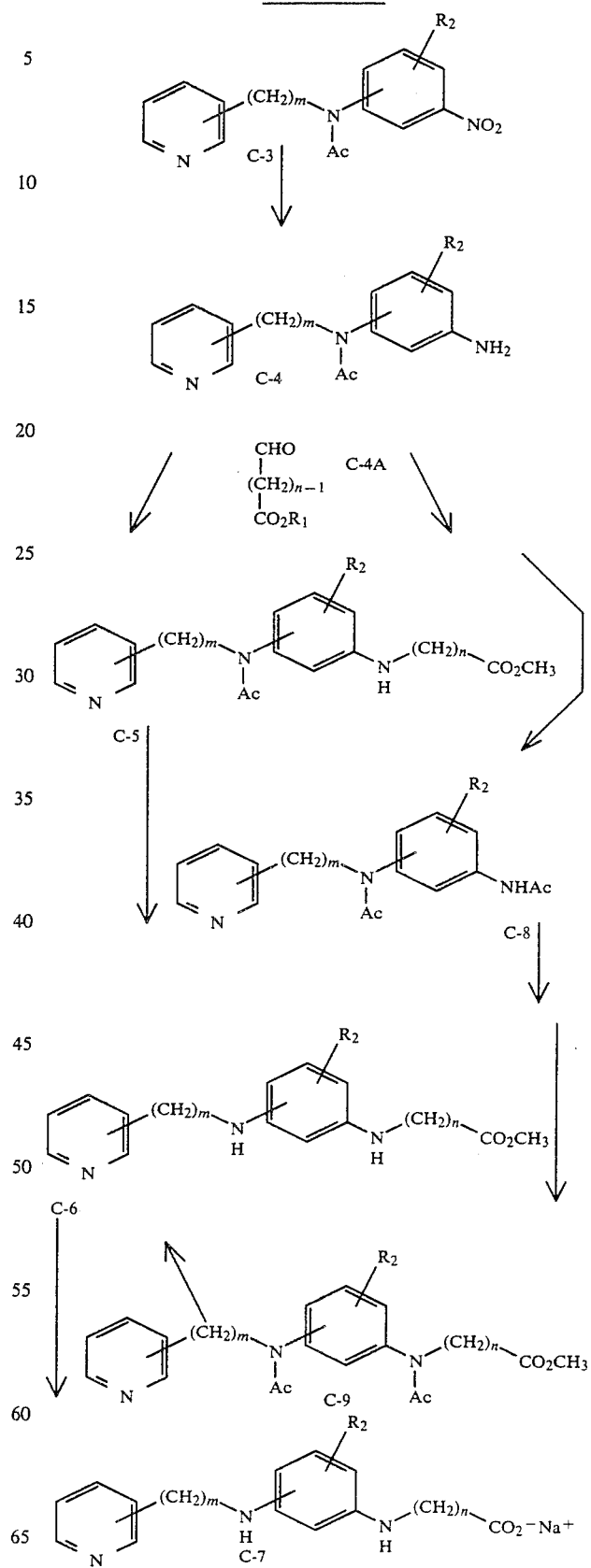
I claim:

1. A compound of the Formula I,

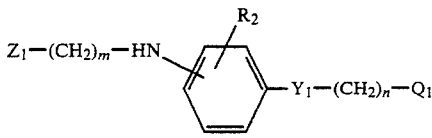

or a pharmacologically acceptable acid addition salt thereof,
wherein $Z_1$ is 2-, 3-, or 4-pyridyl;
wherein $Z_1$—$(CH_2)_m$—NH— is attached ortho, meta or para to —$Y_1$—$(CH_2)_n$—$Q_1$;
wherein $Y_1$ is
  (a) —O—,
  (b) —S—,
  (c) —$NR_3$—, or
  (d) a valence bond;
wherein $R_2$ is
  (a) hydrogen,
  (b) hydroxy,
  (c) methoxy,
  (d) acetoxy,
  (e) fluoro,
  (f) chloro,
  (g) bromo,
  (h) methyl,
  (i) trifluoromethyl,
  (j) dimethylamino,
  (k) nitro,
  (l) mercapto, or
  (m) methylmercapto;
wherein $Q_1$ is
  (a) —$CO_2R_1$, or
  (b) 1-tetrazolyl;
wherein $R_1$ is
  (a) hydrogen,
  (b) a pharmacologically acceptable cation,
  (c) ($C_1$-$C_{12}$) alkyl,
  (d) ($C_3$-$C_{10}$) cycloalkyl,
  (e) ($C_7$-$C_{12}$) aralkyl,
  (f) phenyl,
  (g) phenyl mono-, di-, or trisubstituted by chloro ($C_1$-$C_3$) or alkyl,
  (h) or phenyl para-substituted by
    (1) —NHCO—$R_{25}$,
    (2) —O—CO—$R_{26}$,
    (3) —CO—$R_{24}$,
    (4) —O—CO—(p—Ph)—$R_{27}$, or
    (5) —CH=N—NH—CO—$NH_2$;
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy, $R_{27}$ is hydrogen or acetamido, and —(p—Ph) is 1,4-phenylene;
wherein m is an integer from one to 6, inclusive;
wherein n is an integer from zero to 6, inclusive, with the proviso that n is zero only when $Y_1$ is a valence bond with the further proviso that when $Y_1$ is a valence bond, n is zero, $Q_1$ is $CO_2R_1$, and $R_1$ is hydrogen, alkyl or a pharmacologically acceptable cation, $R_2$ is hydroxy.

2. A compound of claim 1, wherein $Y_1$ is a valence bond; n is zero; m is 1.

3. A compound of claim 1, wherein $Y_1$ is —O—; m is 1; and $Q_1$ is —$CO_2R_1$.

4. A compound of claim 2, wherein $R_1$ is hydrogen or methyl.

5. A compound of claim 2, wherein $R_1$ is a pharmacologically acceptable cation selected from the group consisting of sodium, potassium, and calcium.

6. A compound of claim 3, wherein $R_1$ is hydrogen or methyl and $R_2$ is hydrogen, hydroxy, methoxy, or acetoxy.

7. A compound of claim 3, wherein $R_1$ is hydrogen or methyl, and $R_2$ is fluoro or trifluoromethyl.

8. A compound of claim 3, wherein $R_1$ is a pharmacologically acceptable cation selected from the group consisting of sodium, potassium, and calcium, and $R_2$ is hydrogen, hydroxy, methyl, or acetoxy.

9. A compound of claim 3, wherein $R_1$ is a pharmacologically acceptable cation selected from the group consisting of sodium, potassium, and calcium, and $R_2$ is fluoro or trifluoromethyl.

10. 4-(3-Pyridinylmethylamino)salicyclic acid, methyl ester, a compound of claim 4.

11. 4-(3-Pyridinylmethylamino)salicyclic acid, sodium salt, a compound of claim 5.

12. 5-(3-Pyridinylmethylamino)salicyclic acid, methyl ester, a compound of claim 4.

13. 5-(3-Pyridinylmethylamino)salicyclic acid, sodium salt, a compound of claim 5.

14. 5-(2-Pyridinylmethylamino)salicyclic acid, methyl ester, a compound of claim 4.

15. 5-(2-Pyridinylmethylamino)salicyclic acid, sodium salt, a compound of claim 5.

16. A compound of claim 1 selected from the group consisting of
5-(4-pyridinylmethylamino)salicylic acid, methyl ester;
5-(4-pyridinylmethylamino)salicylic acid, sodium salt;
[4-(3-pyridinylmethylamino)-2-methyl-phenoxy]-acetic acid, methyl ester;
[4-(3-pyridinylmethylamino)-2-methyl-phenoxy]-acetic acid, sodium salt;
[4-(3-pyridinylmethylamino)thiophenoxy]-acetic acid, methyl ester;
[5-(3-pyridinylmethylamino)thiophenoxy]-acetic acid, sodium salt;
5-(3-pyridinylmethylamino)-2- hydroxyphenylamino acetic acid, methyl ester;
5-(3-pyridinylmethylamino)-2-hydroxyphenylamino acetic acid, sodium salt;
5-(3-pyridinylmethylamino)-2-hydroxyphenylamino acetic acid, methyl ester.

* * * * *